(12) United States Patent
Kim (10) Patent No.: US 7,475,797 B2
(45) Date of Patent: *Jan. 13, 2009

(54) LIQUID SUPPLY APPARATUS

(75) Inventor: Yong-Nyun Kim, Seoul (KR)

(73) Assignee: E-WHA Fresenius Kabi Inc., Gunpo-si (KR)

( * ) Notice: Subject to any disclaimer, the term of this patent is extended or adjusted under 35 U.S.C. 154(b) by 445 days.

This patent is subject to a terminal disclaimer.

(21) Appl. No.: 10/503,930

(22) PCT Filed: Feb. 6, 2003

(86) PCT No.: PCT/KR03/00259

§ 371 (c)(1),
(2), (4) Date: Sep. 9, 2004

(87) PCT Pub. No.: WO03/066138

PCT Pub. Date: Aug. 14, 2003

(65) Prior Publication Data

US 2005/0209562 A1   Sep. 22, 2005

(30) Foreign Application Priority Data

Feb. 8, 2002  (KR) ........................ 10-2002-0007578

(51) Int. Cl.
*A61M 37/00* (2006.01)
(52) U.S. Cl. ................... 222/389; 222/387; 222/399
(58) Field of Classification Search ................ 222/389, 222/387, 399, 401
See application file for complete search history.

(56) References Cited

U.S. PATENT DOCUMENTS

| | | | |
|---|---|---|---|
| 3,182,569 A | 5/1965 | Hieber | |
| 4,666,430 A | 5/1987 | Brown | |
| 4,744,442 A | 5/1988 | Bras et al. | |
| 4,813,937 A | 3/1989 | Vaillancourt | |
| 5,312,389 A | 5/1994 | Theeuwes et al. | |
| 5,397,303 A | 3/1995 | Sancoff et al. | |
| 5,398,850 A | 3/1995 | Sancoff et al. | |
| 5,398,851 A | 3/1995 | Sancoff et al. | |
| 5,522,526 A | 6/1996 | DeLaforcade et al. | |
| 5,553,741 A | 9/1996 | Sancoff et al. | |
| 5,558,255 A | 9/1996 | Sancoff et al. | |
| 5,571,261 A | 11/1996 | Sancoff et al. | |
| 5,578,005 A | 11/1996 | Sancoff et al. | |
| 5,588,556 A | 12/1996 | Sancoff et al. | |

(Continued)

FOREIGN PATENT DOCUMENTS

CN      2338019 Y      9/1999

(Continued)

*Primary Examiner*—J. Casimer Jacyna
(74) *Attorney, Agent, or Firm*—Sughrue Mion, PLLC (57) ABSTRACT

A liquid supply apparatus is provided. The liquid supply apparatus has a cylinder, a piston and a gas supply apparatus. The cylinder is provided with a head portion with outlet. The cylinder has a rear end opened. The piston is inserted into the cylinder. The piston moves along the longitudinal direction of the cylinder so as to supply liquid contained in the cylinder. The gas supply apparatus generates and supplies gas to push the piston. The piston has a pair of sealing ring. The sealing ring has a base attached to a body of the piston and a outer wing connected to the base. The gas supply apparatus has a gas pressure regulator.

21 Claims, 8 Drawing Sheets

U.S. PATENT DOCUMENTS

| | | | |
|---|---|---|---|
| 5,700,245 A | 12/1997 | Sancoff et al. | |
| 5,766,147 A | 6/1998 | Sancoff et al. | |
| 5,992,700 A | 11/1999 | McGlothlin et al. | |
| 6,745,920 B2 * | 6/2004 | Gupta | 222/387 |
| 6,786,365 B2 * | 9/2004 | Kim | 222/389 |
| 6,964,356 B2 * | 11/2005 | Kim | 222/389 |

FOREIGN PATENT DOCUMENTS

| | | |
|---|---|---|
| EP | 0 385 916 A2 | 9/1990 |
| JP | S63-142470 | 9/1988 |
| JP | 02-102664 A | 4/1990 |
| JP | H02-130464 | 10/1990 |
| JP | H03-110264 | 11/1991 |
| JP | 04-312469 A | 11/1992 |
| JP | 8-238316 A | 9/1996 |
| JP | 9-500546 A | 1/1997 |
| KR | 98-24858 Y1 | 7/1998 |
| KR | 20-0150725 Y1 | 11/1998 |
| KR | 10-0262930 B1 | 1/1999 |
| KR | 2000-0010499 A | 2/2000 |
| KR | 20-0205619 Y1 | 12/2000 |
| KR | 2001-0039742 A | 5/2001 |
| KR | 2001-0069790 A | 7/2001 |
| KR | 2001-0089470 A | 10/2001 |
| WO | WO 94/26329 A1 | 11/1999 |

* cited by examiner

LIQUID SUPPLY APPARATUS

This is a National Stage Application under 35 U.S.C. § 371 of PCT/KR03/00259 filed Feb. 6, 2003, which claims benefit of Korean Patent Application No. 2002/7578 filed on Feb. 8, 2002, all of which are incorporated herein by reference.

TECHNICAL FIELD

The present invention relates to a liquid supply apparatus, and more particularly, to a liquid supply apparatus constructed so that liquid such as infusion medicine is supplied in a constant quantity per unit time.

BACKGROUND ART

In the field of medicine, there are certain types of medicine such as anodynes or antitumor agents that should be infused into patients over a long period of time, and these types of medicine generally require infusions thereof into the patients in substantially constant quantities per unit time. There have been apparatuses, which use common syringes, for infusing medicine into patients in a constant quantity per unit time, and the syringes are mounted in the apparatuses so that plungers of the syringes can be gradually pushed. Due to the large sizes of the apparatuses, it is unsuitable for carrying by the patients.

There has been proposed a liquid supply apparatus capable of being carried by a patient. The conventional portable liquid supply apparatus has a structure in which a resilient bladder made of rubber material is provided in a cylindrical chamber. An inlet and an outlet are formed on the resilient bladder. The bladder inflates as medicine is infused through the inlet. The medicine gradually draws off through the outlet to which an elongated tube is attached. The medicine (for infusion) is discharged in a small amount and infused into the vein of a patient. In the liquid supply apparatus, the resilient bladder may cause the following problem. Upon manufacture of the resilient bladder, inferior goods in which the thickness of the bladder is not uniform or fine holes are formed thereon may be produced. The inferiority affects the resiliency of the bladder which in turn cannot have the desired resiliency. If this is the case, it is difficult to keep an infusion quantity per unit time constant.

There has also been proposed a liquid supply apparatus that uses a bladder and an elastic body. In the resilient bladder or elastic body, its resiliency or elasticity may vary in accordance with the quantity of the medicine contained therein. An external force (the restoring force of the elastic body) on liquid flow may also be different at early and final periods of infusion. This is because the restoring force of the elastic body varies according to the amount of its deformation.

The present inventor has proposed a liquid supply apparatus with a new structure to overcome the aforementioned problems. In the newly proposed liquid supply apparatus, a piston is pushed within a cylinder by the pressure of gas generated in the apparatus. The piston drives the supply of infusion medicine to the patient. An example of the liquid supply apparatus is disclosed in International Publication No. WO 02/11791. The liquid supply apparatus of the present inventor has a superior advantage of being easily carried, maintaining a constant quantity of infusion and the like. Nevertheless, continuous improvement will be made therein in the same manner as other superior technologies.

SUMMARY OF THE INVENTION

An object of the present invention is to provide a liquid supply apparatus with an improved structure.

A specific object of the present invention is to provide a sealing ring structure of a piston for effectively preventing leakage of liquid (an infusion medicine) contained in a cylinder.

Another object of the present invention is to provide a structure for effectively preventing leakage of gas in a case where the gas pressure is used to drive the piston.

A further object of the present invention is to provide a pressure regulating structure that operates effectively.

A still further object of the present invention is to provide a structure capable of preventing a phenomenon wherein the piston is pushed before using the liquid supply apparatus.

A still further object of the present invention is to provide a structure for enabling a gas supply apparatus to securely perform its function.

According to the present invention, there is provided a liquid supply apparatus, comprising an elongated cylinder including a head portion with an opening, and an open rear portion; a piston which is inserted into the cylinder and hermetically divides an inner space of the cylinder into a liquid compartment on the side of the head portion and a gas compartment on the side of the rear portion; and a gas supply apparatus constructed to supply the gas compartment with gas and connected to the rear portion of the cylinder, whereby the piston is moved toward the head portion when the gas is supplied to the gas compartment.

The piston may comprise a body and a sealing ring which surrounds the body and is in contact with an inner surface of the cylinder, and the sealing ring comprises an inner base fixed to the body and an outer wing which is connected to the base and is in contact with the inner surface of the cylinder. The outer wing may be inclined with respect to a wall of the cylinder.

The piston may comprise at least two sealing rings, and the outer wing of one of the sealing rings on a side of the liquid compartment extends toward the liquid compartment and the outer wing of the other sealing ring on a side of the gas compartment extends toward the gas compartment.

The body may be provided with an annular groove, and the base of the sealing ring may be fitted into the groove. The sealing ring on the side of the liquid compartment and the sealing ring on the side of the gas compartment may be sealing rings with a substantially identical dimension, and a radius of the bottom of the groove in the piston body into which the sealing ring on the side of the gas compartment is fitted may be larger than that of the bottom of the groove into which the sealing ring on the side of the liquid compartment is fitted. The outer wing may be configured such that a tip thereof does not extend beyond a distal end of the base.

The head portion of the cylinder may include a truncated conical projection extending into the cylinder, the projection may be formed with an opening, and the piston may be provided with a truncated conical recess for accommodating the portion.

In one embodiment, the gas supply apparatus comprises an outer wall and a partition connected to the outer wall so as to define a gas supply chamber by the outer wall and the partition, the gas compartment of the cylinder and the gas supply chamber are divided by the partition, and the partition is provided with a through-hole through which the gas supply chamber and the gas compartment communicate with each other.

The outer wall and the rear portion of the cylinder may be fitted into or around and coupled with each other, and an annular groove is provided in one of fitted contact surfaces thereof, whereby upon coupling of the outer wall and the rear portion of the cylinder using an adhesive, a surplus of the adhesive is received by the annular groove.

The outer wall may comprise an insertion portion tightly fitted into the cylinder and bonded to an inner surface of the cylinder using an adhesive, an exposed portion exposed outside of the cylinder, and a stepped portion connected to an outer wall of the exposed portion radially outward from an outer wall of the insertion portion, and an edge between the insertion portion and the stepped portion may be provided with an annular groove.

The partition of the gas supply apparatus may be provided with a bore through which the gas compartment and the outside of the cylinder communicate with each other, and the gas supply apparatus may further comprise a pressure regulator provided in the bore. The bore may be cylindrical and connected to the gas compartment through a connection passage formed in the bottom of the bore. The pressure regulator may comprise a sealing ring which surrounds the connection passage, is fixed to the bottom, and has an end protruding from the bottom, an opening/closing member including a contact wall with a contact surface which selectively comes into contact with or is separated from the end of the sealing ring, an inner wall axially extending from a central portion of the contact wall, and a conical slant wall protruding from an end of the inner wall to a side opposite to the connection passage, thereby moving in an axial direction of the bore, and an elastic member for urging the opening/closing member toward the sealing ring.

A protruding tube surrounding the connection passage and axially protruding from the bottom may be provided in the bore, and the inner wall of the opening/closing member may surround the protruding tube. A guide structure for linear movement of the opening/closing member may be provided between the protruding tube or the connection passage and the inner wall of the opening/closing member. The opening/closing member may further comprise an axially extending outer wall, and a guide structure for linear movement of the opening/closing member is provided between the outer wall and the bore. A stroke of the opening/closing member may be limited to no more than 2 mm. The sealing ring may be fixed by being fitted into a groove formed in the bottom, and a tip of a portion of the sealing ring protruding from the groove may be rounded.

Meanwhile, the partition of the gas supply apparatus may be provided with a passage through which the gas compartment and the outside of the cylinder communicate with each other, a one-way valve may be provided in the passage, and the one-way valve may allow gas to flow into the cylinder but prevents gas from flowing out.

In another embodiment, the gas supply chamber of the gas supply apparatus comprises a first chamber for containing a liquid material and a second chamber for containing a solid material which generates gas through a reaction with the liquid material, and a breakable separation structure is provided between the first and second chambers. An elastic member for urging the solid material toward the separation structure may be provided in the first chamber.

The separation structure may comprise a first partition which surrounds a passage between the first and second chambers and is provided with an annular groove, and a second partition of which a rim is fitted into the annular groove of the first partition. A sealing ring may be provided between the first and second partitions.

In a further embodiment, the outer wall of the gas supply apparatus further comprises a cover as a separate member, and the first chamber is defined in the cover.

The cover may comprise a peripheral wall fitted around the outer wall, and an annular groove may be provided in one of fitted contact surfaces thereof, whereby upon coupling of the cover and the outer wall using an adhesive, an adhesive receiving space for collecting and receiving a surplus of the adhesive is provided.

The cover may comprise a peripheral wall and an inner sidewall extending parallel to and spaced apart from the peripheral wall at an outer periphery of the cover, whereby an end of a sheet for filtering gas is placed between the peripheral wall and the inner sidewall.

BRIEF DESCRIPTION OF THE DRAWINGS

These and other objects and features of the present invention will be apparent to those skilled in the art upon reading and understanding the following detailed description of preferred embodiments of the present invention with reference to the accompanying drawings in which:

FIGS. 3(a) and (b) are sectional views of a pressure regulator constructed by inserting the insert members for pressure regulation into a gas supply apparatus in the liquid supply apparatus of FIG. 1, wherein (a) shows the state where an opening/closing member is closed and (b) shows the state where the opening/closing member is opened;

DETAILED DESCRIPTION OF THE EMBODIMENTS

Figure 1:
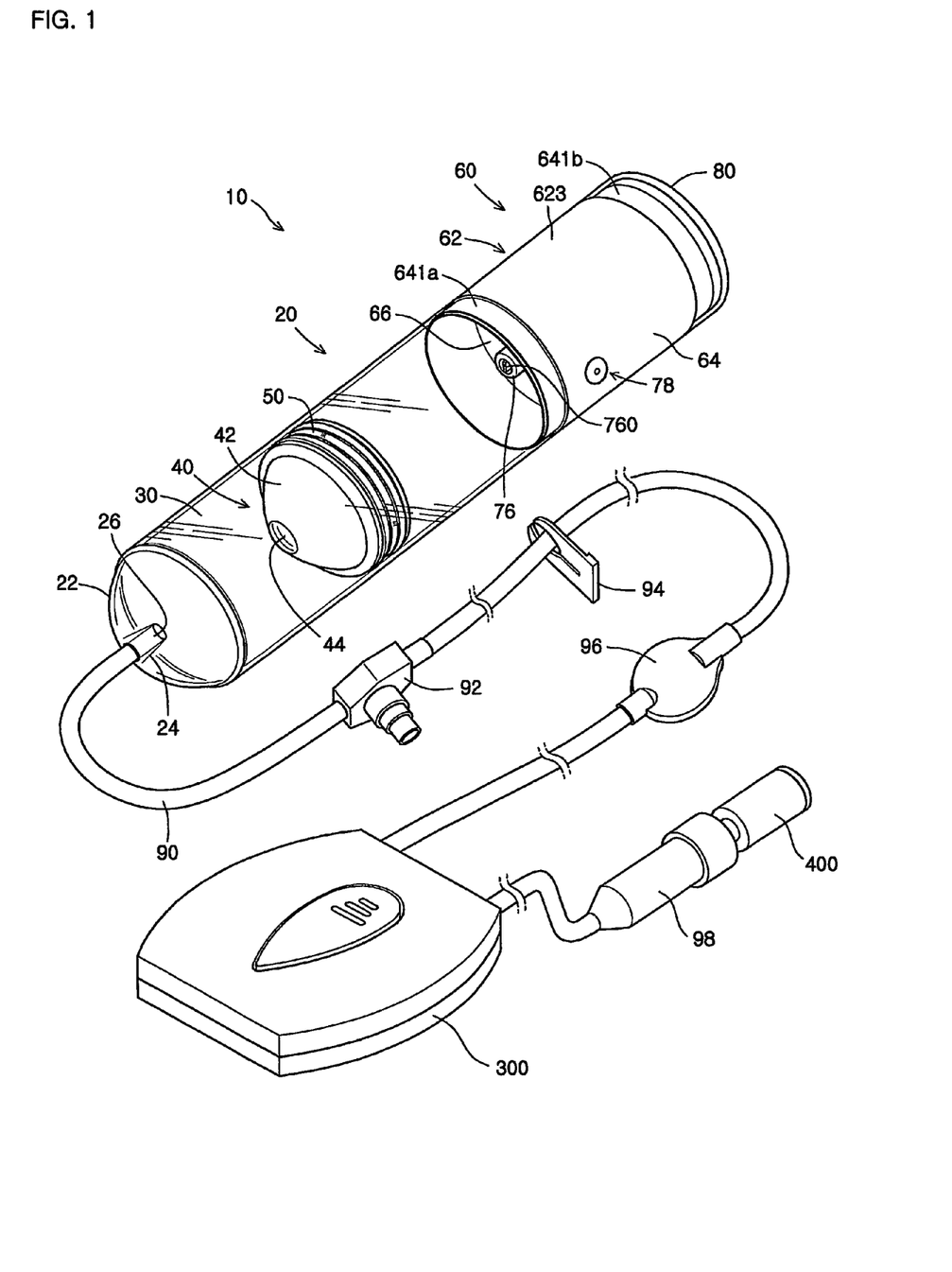
FIG. 1 is a perspective view of a liquid supply apparatus according to an embodiment of the present invention.

FIG. 1 is a perspective view of a liquid supply apparatus according to an embodiment of the present invention. Referring to FIG. 1, the liquid supply apparatus 10 comprises a cylinder 20, a piston 40 disposed within the cylinder 20, and a gas supply apparatus 60 disposed at an end of the cylinder 20. A tube 90 is connected to a front end of the cylinder 20.

Figure 2:
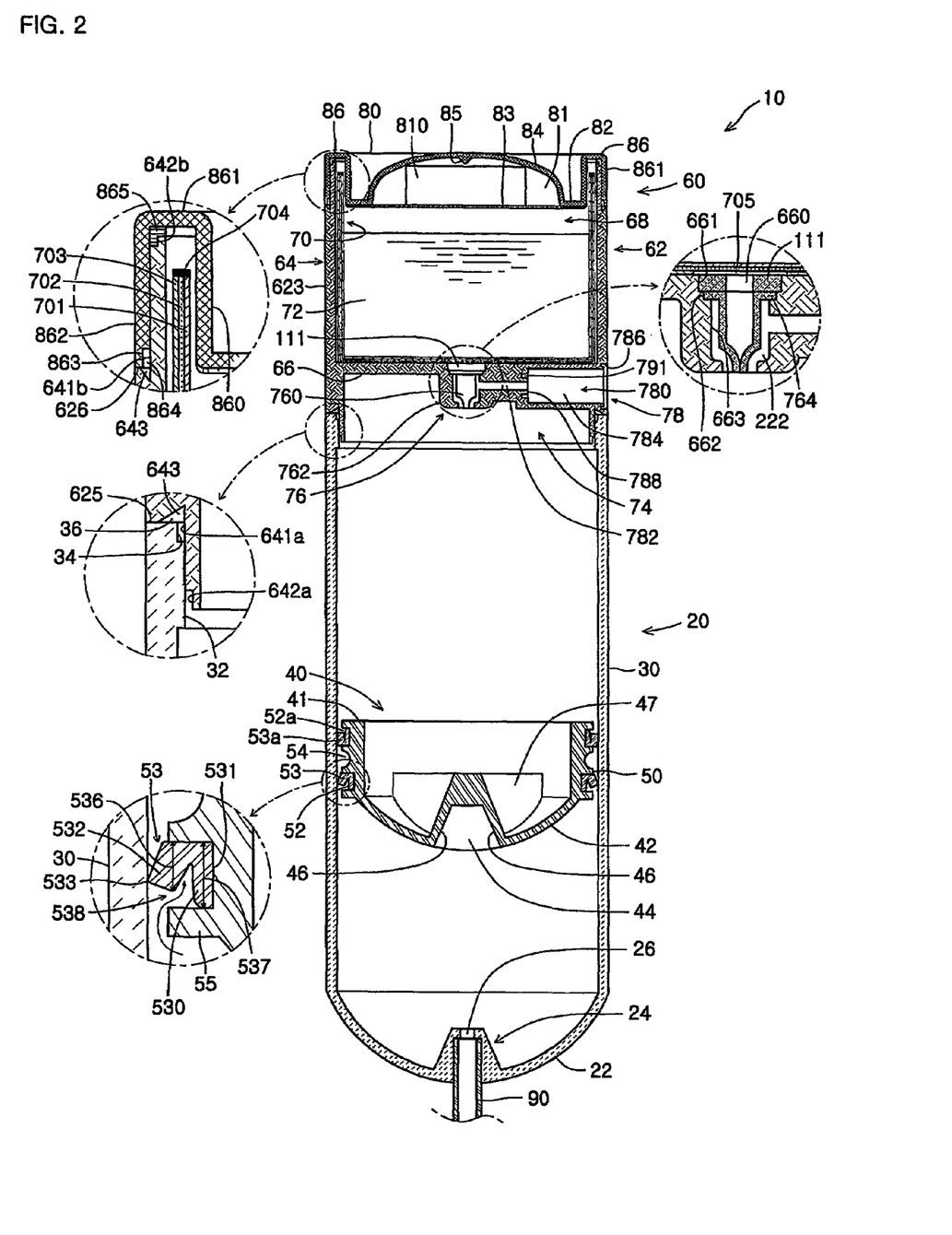
FIG. 2 is a sectional view of the liquid supply apparatus of FIG. 1, with insert members for pressure regulation excluded.

Referring to FIGS. 1 and 2, the cylinder 20 is hollow and cylindrical. The cylinder 20 is generally manufactured by molding transparent plastic resin material. The cylinder 20 comprises a head portion 22, and a cylindrical sidewall 30 extending lengthwise rearward from the head portion 22. The head portion 22 of the cylinder 20 has a generally hemispherical shape and protrudes outward (however, the present invention is not limited thereto). A projection 24, which protrudes into the cylinder 20 and preferably takes the shape of a truncated cone, is formed at the center of the head portion 22. The projection 24 is longitudinally formed with a through-hole 26 at the center thereof. An end of the tube 90 is inserted into and fixed to the through-hole 26. Since the projection 24 protrudes inward, risk that it is damaged by external factors is remarkably reduced. With such a structure, possibility that the tube 90 will be bent is reduced.

Referring to FIG. 1, the tube 90 has various components required for medicine infusion, such as a supply valve member 92 for medicine infusion, a clamp 94 for preventing medicine from being infused when necessary, and a filter 96 for filtering out foreign materials from the medicine. An infusion quantity adjustor 300 is also installed at the tube 90. The infusion quantity adjustor 300 adjusts an infusion quantity of the medicine to be supplied in various ways. One of the various ways is to increase the infusion quantity of the medicine when required. A distal end 98 of the tube 90 is constructed to be connected, for example, to an infusion needle inserted into or another tube communicating with a catheter stuck into a body of a patient. Before use thereof, the distal end 98 is plugged by a cap 400 as shown in FIG. 1.

Referring to FIGS. 1 and 2, a rear end of the sidewall 30 of the cylinder 20 is open and the piston 40 is inserted into the cylinder 20 through the open rear end of the sidewall 30. Then, the gas supply apparatus 60 is fitted into the open rear end and fixed to the cylinder 20. Referring to FIG. 2, an inner wall portion at the rear end of the sidewall 30 of the cylinder 20 is provided with an inner wall projection 32 taking the shape of a band formed by causing the inner wall portion to protrude radially inward. A rear end of the inner wall projection 32 is provided with an inner wall depression portion 34 formed in such a manner that a portion of the inner wall projection is depressed. This structure is to ensure effective coupling with the gas supply apparatus 60, which will be described in detail later. Although it is not shown, a scale is printed onto an external surface of the sidewall 30 so that the amount of medicine contained or remaining in the cylinder 20 can be recognized.

Referring to FIGS. 1 and 2, the piston 40 inserted into the cylinder 20 comprises a body 41 and sealing rings 53 fitted around an outer surface of the body 41. The piston body 41 comprises a leading end portion 42, and a cylindrical sidewall 50 extending rearward from the leading end portion 42. The leading end portion 42 of the piston is formed to be hemispherical such that it generally conforms to an inner side of the head portion 22 of the cylinder 20. The center of the leading end portion 42 is provided with a recess 44 with a slant surface 46 that is inclined to generally conform to the shape of the projection 24 of the cylinder 20. The projection 24 of the cylinder 20 is fitted into the recess 44. The piston body 41 is preferably manufactured by molding plastic resin material. A rib 47 is provided on an inner side of the piston body 41 for maintaining rigidity thereof.

The sidewall 50 of the piston body 41 is provided with two annular insertion grooves 52, 52a extending circumferentially thereon and a middle groove 54 formed between the two insertion grooves 52, 52a. The insertion grooves 52, 52a have a generally rectangular cross section. The sealing rings 53, 53a to be described in detail later are fitted into the two insertion grooves 52, 52a, respectively. The rear insertion groove 52a of the two insertion grooves 52, 52a is slightly shallower than the insertion groove 52 adjacent to the leading end portion 42. This is to maintain balance against a difference in pressure when the sealing ring 53 adjacent to the leading end portion and the rear sealing ring 53a are simultaneously subjected to an identical pressure, and thus, prevents the any leakage of gas. At this time, the rear insertion groove 52a is shallower by 0.05 to 0.5 mm (preferably, 0.1 mm) than the insertion groove 52 adjacent to the leading end 42 (that is, a radius of the bottom of the rear insertion groove is larger than that of the bottom of the front insertion groove). It is also to increase the size of the sealing ring 53a. The middle groove 54 has a generally semi-circular cross section. Such a groove 54 enables materials to be saved and the weight of the piston body 41 to be reduced by removing an unnecessary flesh portion.

Referring to FIG. 2, the sealing rings 53, 53a are annular rings that are generally V-shaped in cross section to be bent in the middles thereof. Each of the sealing rings 53, 53a is V-shaped by including an annular base 530 that is formed on an inner side of the sealing ring and fixedly inserted into one of the insertion grooves 52, 52a provided in the sidewall 50 of the piston body 41, and an annular outer wing 532 that is formed on an outer side of the sealing ring and comes into contact with the cylinder 20. The outer wing 532 is connected to one side of the base 530 while forming an acute angle therebetween. The base 530 is configured so as to be tightly fitted into one of the insertion grooves 52, 52a.

In the outer wing 532, a connection bent in the form of a "V" or the outer ring itself can be deformed so that a gap between the base 530 and the outer wing 532 can be reduced. A width of the base 530 is determined to be fixedly inserted into the insertion groove 52. A vertical width (distance between the connection and tip) 536 of the outer wing 532 in an axial direction (a longitudinal direction of the cylinder) is preferably determined to be slightly shorter than a width 537 of the base 530. This is to prevent the outer wing 532 from being held in the groove 52. Further, the length from the flat bottom 531 of the base 530 to a contact portion 533 of the outer wing 532 is larger than the depths of the insertion grooves 52, 52a. The contact portion 533, which comes into contact with the cylinder 20 and is positioned at an outermost portion of the outer wing 532, is rounded.

One of the sealing rings 53, 53a taking the aforementioned shape is fitted into the insertion groove 52 adjacent to the leading end of the piston body 41. At this time, the base 530 is inserted into and fixed to the insertion groove 52 so that the tip of the outer wing 532 is directed to the medicine. The contact portion 533 of the sealing ring 53 protrudes outside of the piston body 41 and comes into contact with the sidewall 30 of the cylinder 20. At this time, a space 538 between the base 530 and the outer wing 532 is open toward a space containing the infusion medicine. Pressure of the medicine is transmitted to the open space 538. The pressure urges the outer wing 532 against the sidewall 30 of the cylinder 20 to improve the sealing effect. Further, since the contact portion 533 of the sealing ring 53 is rounded, it can be easily slidably moved along the sidewall 30 of the cylinder 20 despite a curve in the sidewall. On the other hand, the sealing ring 53a can be considered to be the same as the aforementioned sealing ring 53 in their constitutions except that it is fitted into the rear insertion groove 52a so that the open space is directed rearward as shown in FIG. 2. These sealing rings 53, 53a are preferably made of elastic rubber material.

Referring to FIGS. 1 and 2, the gas supply apparatus 60 is cylindrical, and an end thereof is partially inserted into the open rear end of the cylinder and fixed to the cylinder 20. The gas supply apparatus 60 supplies gas to the cylinder 20 so as to cause the piston 40 to move at a substantially constant rate toward the head portion 22 of the cylinder 20 by using the gas pressure. The gas supply apparatus 60 comprises a body 62, and a cover 80 for covering an end of the body 62. The body 62 includes a cylindrical sidewall 64, and a partition 66 disposed therein. The sidewall and the cover define an outer wall of the gas supply apparatus. The sidewall 64 of the body 62 includes a cylinder insertion portion 641a and a cover insertion portion 641b provided at both ends of the sidewall 64 so that the sidewall can be fitted into the cylinder 20 and the cover 80, and an exposed portion 623 between the two insertion portions 641a, 641b. The cylinder insertion portion 641a and the cover insertion portion 641b are configured such that the outer wall surfaces thereof are depressed radially inward as opposed to an outer wall surface of the exposed portion 623. A first stepped portion 625 with a groove 643 provided at a radially inward portion thereof is formed between the cylinder insertion portion 641a and the exposed portion 623. A free end of the cylinder insertion portion 641a is provided with an outer wall depression portion 642a formed in such a manner that the outer wall surface thereof is again depressed radially inward. A second stepped portion 626 with a groove 643 provided at a radially inward portion thereof is formed between the cover insertion portion 641b and the exposed portion 623. A free end of the cover insertion portion 641b is provided with an outer wall depression portion 642b formed in such a manner that the outer wall surface thereof is again depressed radially inward.

The coupling of the body 62 with the cylinder 20 is achieved through bonding of the cylinder insertion portion 641a of the body 62 to the inner wall projection 32 of the cylinder 20 using an adhesive. Generally, the adhesive is applied to a wall surface of the cylinder insertion portion 641a and the body 62 is then fitted into the cylinder so that they are bonded. The adhesive can be pushed and moved by the inner wall projection 32 of the cylinder 20. The pushed and moved adhesive is collected in the inner wall depression portion 34 of the cylinder 20 or in the small space 36 where the groove 643 of the stepped portion 625 of the body 62 is formed. Further, some of the adhesive is applied even between the outer wall depression portion 642a of the body 62 and the inner wall projection 32 of the cylinder 20. Since the adhesive cures to perform the bonding, a surplus of the adhesive cannot flow out. Thus, the bonded portions are clean and the sealing effect is improved. The coupling of the cover 80 with the body 62 will be described in detail later.

The body 62 is divided into a first cavity 68 directed to the cover 80 and a second cavity 74 directed to the cylinder 20 by the sidewall 64 and the partition 66. The first and second cavities 68, 74 communicate with each other through a through-hole 660 provided in the center of the partition 66. The first cavity 68 is provided with a flexible multi-layered gas-permeable sheet 70 over the inner periphery and bottom of the first cavity. The sheet functions as a gas-permeable but liquid-impermeable filter. The sheet 70 is formed by sequentially laminating three layers, that is, a liquid-impermeable but gas-permeable membrane 701, a gas passage sheet 702, preferably made of nonwoven fabric sheet of synthetic fiber, capable of passing or retaining gas to form a gas passage, and a flexible liquid- and gas-impermeable film 703. The film 703 is located on a side facing the bottom and sidewall of the first cavity 68. As for the film 703, it is possible to use a normal soft transparent vinyl sheet. Instead of the nonwoven fabric sheet, it is also possible to use a pliable and porous foam body such as a sponge. The three layers are coupled together at an outermost bonding portion 704 by preferably applying heat and pressure thereto. The film 703 is formed with an aperture 705 at the center of the bottom. The aperture 705 communicates with the through-hole 660 in the bottom. A portion of the film 703 around the aperture 705 is attached to the bottom of the first cavity 68.

A liquid material 72 is accommodated in the first cavity 68 in which the sheet 70 exists. The liquid material 72 may be an L-tartaric acid ($C_4H_6O_6$) or citric acid solution that is harmless to a human body. The L-tartaric acid ($C_4H_6O_6$) or citric acid solution in a liquid phase does not leak downward due to a liquid sealing effect of the sheet 70.

Figure 7:
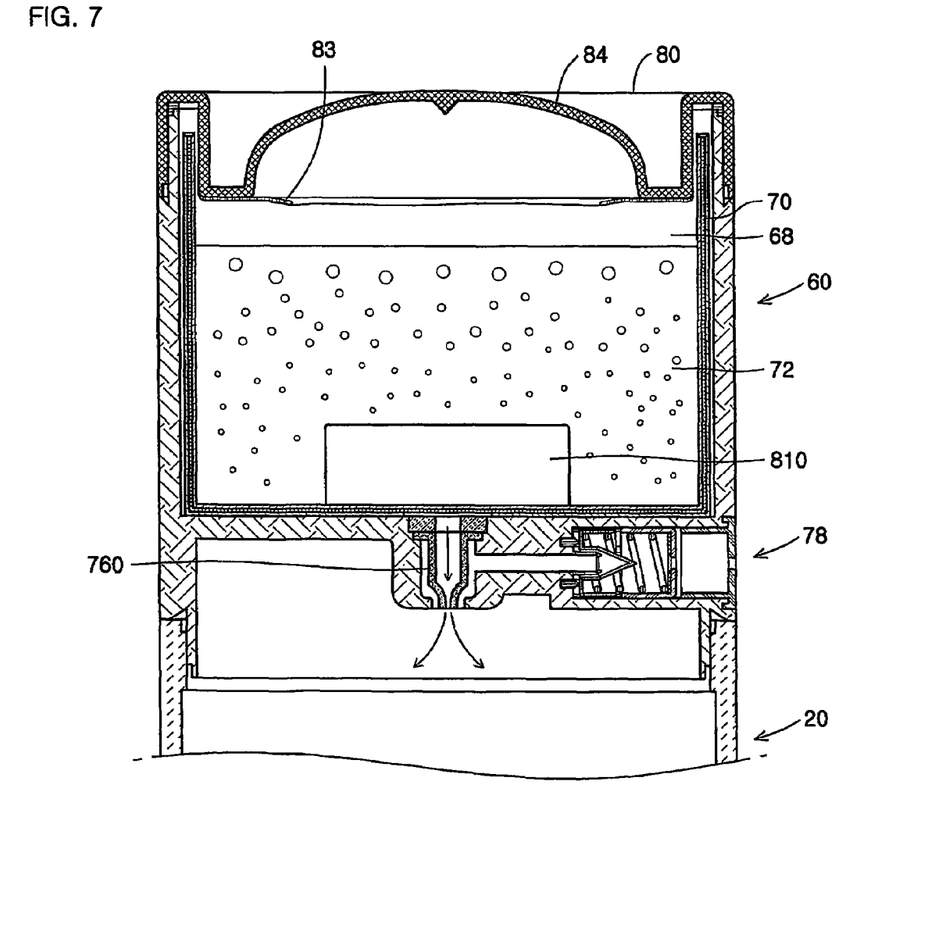
FIG. 7 is a sectional view showing the operation of the gas supply apparatus provided in the liquid supply apparatus of FIG. 1.

Referring to FIGS. 1, 2 and 7, the second cavity 74 is provided with an exhaust portion 76 formed to protrude from a central portion of the partition 66, and a pressure regulator 78 provided between the exhaust portion 76 and the sidewall. The exhaust portion 76 includes a valve fixing ring 111 fitted into the through-hole 660 of the partition 66, a one-way valve 760 connected to the through-hole 660, and a protruding wall 762 that protrudes from the partition 66 to surround the one-way valve 760 with a gap therebetween and defines an exhaust passage 222 therein. The through-hole 660 of the partition 66 is divided into first to third sections 661, 662 and 663 that have different inner diameters. The first section 661 with the largest inner diameter is located on the side of the first cavity 68. The third section 663 with the smallest inner diameter is located on the side of the second cavity 74. The inner diameter of the second section 662 located between the first and third sections 661, 663 is smaller than that of the first section 661 but larger than that of the third section 663.

The one-way valve 760 made of rubber material is hollow and cylindrical. It has one open end, and the other end pursed up for closing. The open end is provided with a stepped portion 764 with an outer diameter larger than that of the other portion, along the circumference thereof. The outer diameter and length of the stepped portion 764 generally correspond to those of the second section 662 of the through-hole 660. The stepped portion 764 of the one-way valve 760 is fitted into the second section 662 of the through-hole 660. The one-way valve 760 is preferably made of rubber material. When gas is supplied and a predetermined pressure is thus applied to the one-way valve 760, the pursed end is opened to serve as a check valve as shown in FIG. 7. An outer diameter of the valve fixing ring 111 generally corresponds to the inner diameter of the first section 661 of the through-hole 660 to be tightly fitted thereinto. The valve fixing ring 111 is tightly fitted into the first section 661 so that the one-way valve 760 is fixed.

Referring to FIGS. 1, 2, 3 and 7, the pressure regulator 78 is constructed by inserting a plurality of insert members into a bore 780 connected from the sidewall 64 of the body 62 to the exhaust passage 222. The bore 780 is connected to the second cavity through a connection passage 782 extending from the exhaust passage 222. The sidewall 64 in which an outermost portion of the bore 780 exists is provided with an annular groove 786 surrounding the circumference of the bore 780. An annular groove 791 into which a sealing ring 79 to be described later is fitted is formed in a boundary stepped-portion 788 between the connection passage 782 and the bore 780. The groove 791 is rectangular in cross section.

Figure 3:
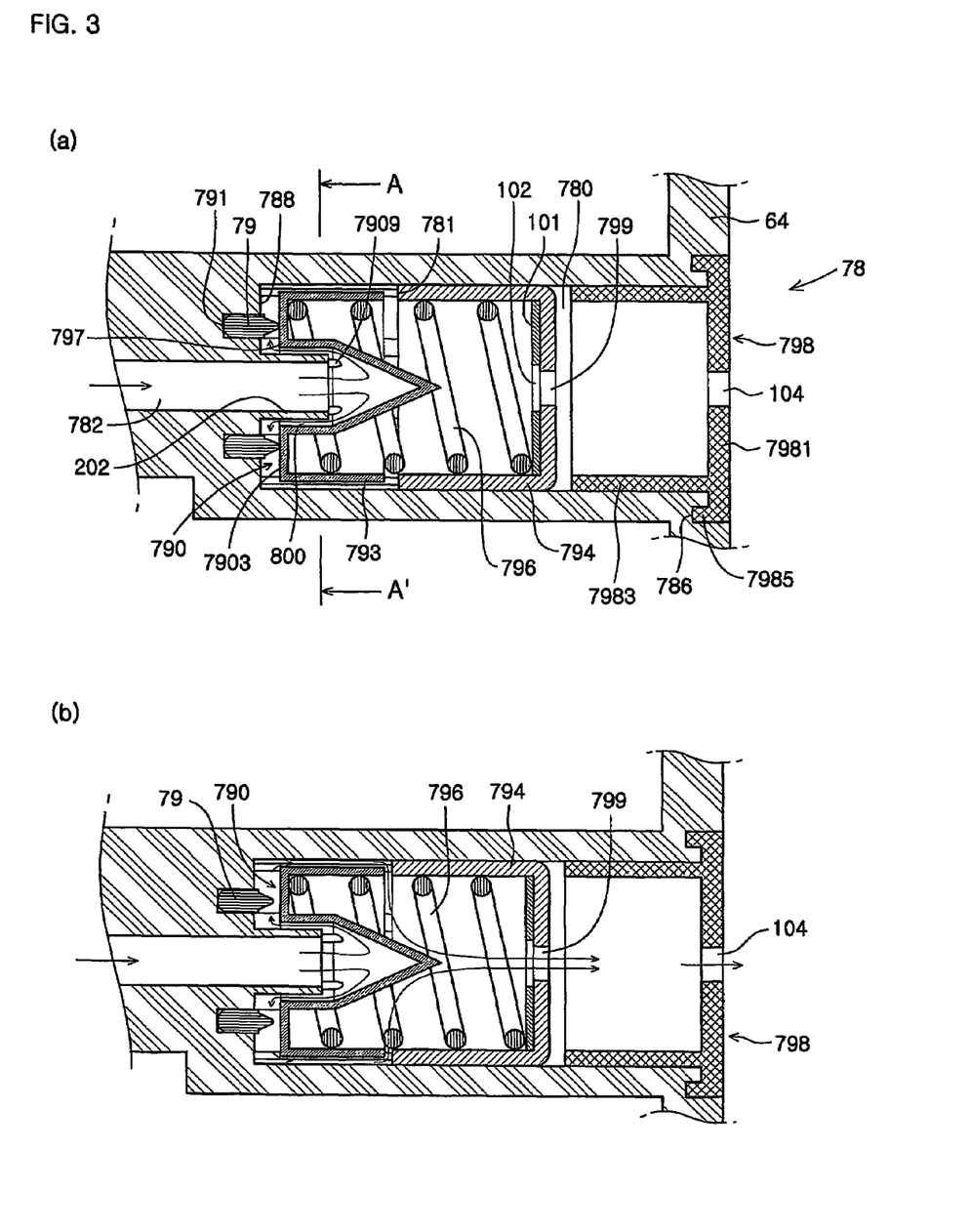

Referring to FIGS. 3(*a*) and 6, a wall surface 783 of the bore 780 is provided with a plurality of protruding support ribs 781 extending from the boundary stepped-portion 788 to a longitudinally middle portion of the bore. As can be clearly seen from FIG. 6, each of the protruding support ribs 781 is semicircular in cross section. The protruding support ribs 781 guide an opening/closing member 790 to be described later. Further, the wall surface 783 of the bore 780 and the opening/closing member 790 are spaced apart from each other by means of the protruding support ribs 781 to provide a gas passing passage 785 therebetween. Meanwhile, a central portion of the boundary stepped-portion 788 is provided with a cylindrical protruding tube 202 extending toward the bore 780 while surrounding the connection passage 782.

Figure 4:
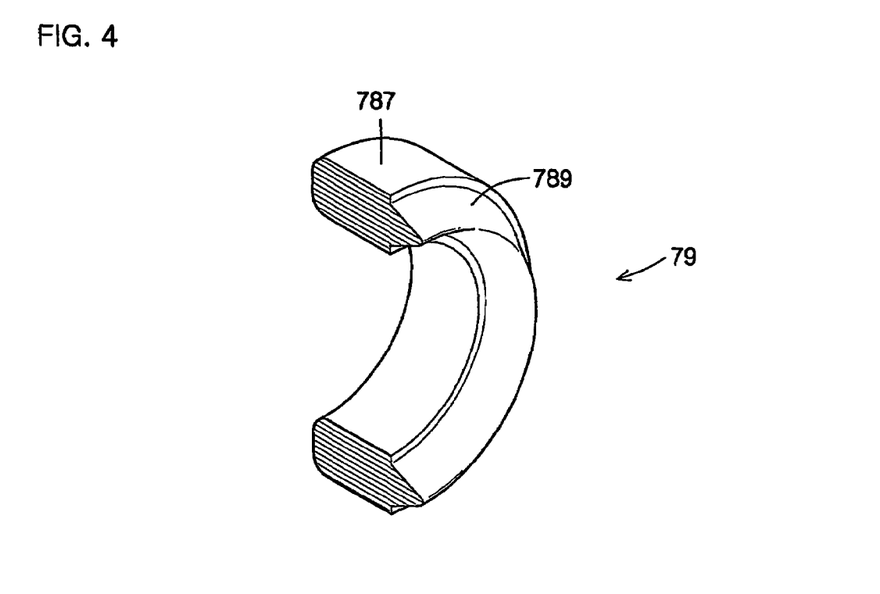
FIG. 4 is a sectional perspective view of a sealing ring of the pressure regulator of FIG. 3.

Referring to FIG. 3(*a*), the insert members to be fitted into the bore 780 include the sealing ring 79, a fixing member 794, an elastic member 796 and a cover member 798. Referring to FIGS. 3(a) and 4, the sealing ring 79 comprises a base 787 fitted into the groove 791, and a contact portion 789 in contact with the opening/closing member 790. The base 787 is generally rectangular in cross section, whereas an edge of the base to be inserted into the groove 791 is rounded. This is to cause air remaining in the groove 791 to be collected around the rounded edge so that the sealing ring 79 can be fully fitted into the groove 791. The contact portion 789 protrudes from the base 787 and extends to have a tapered cross section with a pointed end of which the tip is slightly rounded. The opening/closing member 790, which comes into contact with the contact portion 789 constructed as such, as will be described later, has a reduced contact area therewith, and thus, can sensitively respond to a slight change in pressure.

Figure 5:
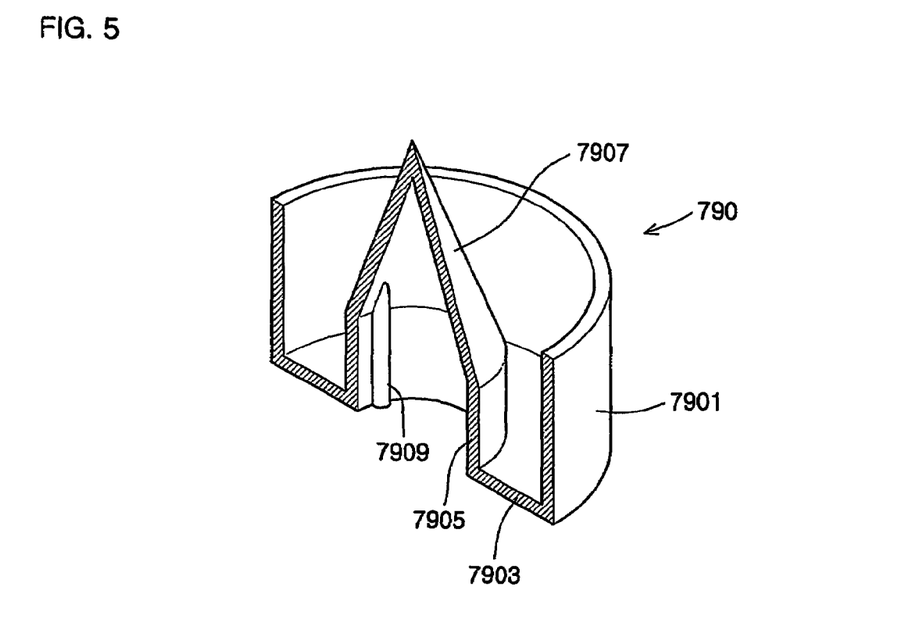
FIG. 5 is a sectional perspective view of the opening/closing member of the pressure regulator of FIG. 3.
Figure 6:
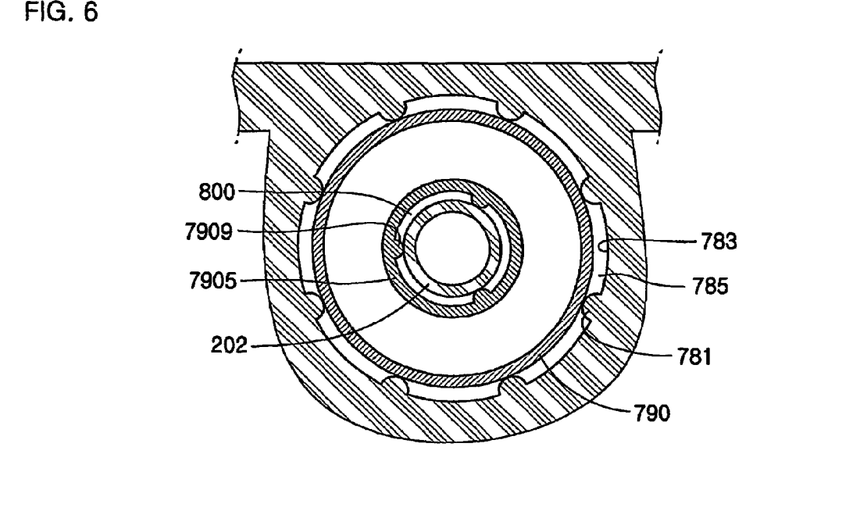
FIG. 6 is a sectional view of the pressure regulator, taken along line A-A' in FIG. 3(a)

Referring to FIGS. 3(a) and 5, the opening/closing member 790 comprises a cylindrical outer wall 7901, a bottom wall 7903, a cylindrical inner wall 7905 extending from a central portion of the bottom wall, and a conical slant wall 7907 extending from the cylindrical inner wall 7905. The protruding tube 202 is received in the cylindrical inner wall 7905. An inner space defined by the cylindrical inner wall 7905 is closed at an end by means of the conical slant wall 7907. An inner diameter of the inner wall 7905 is slightly larger than an outer diameter of the protruding tube 202. Referring to FIGS. 5 and 6, an inner surface of the inner wall 7905 is provided with three ridges 7909 extending in a longitudinal direction of the inner wall 7905 (the present invention is not limited to the three projections). Each of the ridges 7909 has a semicircular cross section of which vertex is in contact with an outer wall of the protruding tube 202. The inner wall 7905 advances by means of the ridges 7909 so as to guide the movement of the opening/closing member 790. Further, the outer wall of the protruding tube 202 and the inner wall 7905 are spaced apart from each other by means of the ridges 7909 to provide a gas passing passage 800.

An outer surface of the bottom wall 7903 is flat and comes into contact with the sealing ring 79. In a state where the opening/closing member 790 is in contact with the sealing ring 79, a distal end of the outer wall 7901 does no reach longitudinal one ends of the protruding support ribs 781 (see FIG. 6) on the wall surface of the bore 780. The opening/closing member 790 is preferably made of synthetic resin (e.g., Teflon, PEEK, PFT, PTFE and the like) that is light in weight and can minimize shrinkage upon molding thereof. With such a configuration, the opening/closing member 790 can be pushed before air pressure beyond a regulation threshold is applied directly to the sealing ring. Thus, the opening/closing member 790 can be moved with smooth air flow. Further, since the center of gravity of the opening/closing member 790 is located at a position near to the conical slant wall in the center axis of the opening/closing member, lateral rocking thereof can be reduced, and thus, its operation is stabilized.

Referring again to FIG. 3(a), a compression coil spring 796 as an elastic member is interposed between the opening/closing member 790 and the fixing member 794, which will be described later. One end of the compression coil spring 796 is confined by being fitted between the outer and inner walls of the opening/closing member 790, preferably snugly fitted into the outer wall, whereas the other end thereof is confined by being fitted into the fixing member 794, so as to urge the opening/closing member 790 toward the sealing ring 79.

Referring still to FIG. 3(a), the fixing member 794 takes the shape of a cylinder with an open end. A hole 799 is provided in the center of the bottom of the fixing member, and a sidewall of the fixing member is in contact with the wall surface of the bore 780. The fixing member 794 is inserted into the bore 780 so that the open end thereof is directed radially inward. The fixing member is fixed to the wall surface of the bore such that the open end of the fixing member is in contact with the longitudinal ends of the protruding support ribs 781. At this time, it can be fixed by using an adhesive or solvent, preferably by using a press-fit method. Upon use of the press-fit method, it is possible to prevent a physical change in characteristics of the fixing member 794 which may occur upon use of the adhesive or solvent. This is advantageous in that it is possible to prevent variances in reference pressure regulated by the pressure regulator 78. It is preferred that the interval between the ends of the fixing member 794 and opening/closing member 790 (i.e., allowable stroke of the opening/closing member) be kept small (e.g., 1 to 2 mm) in a closed state (a contact state of the opening/closing member with the sealing ring). By doing so, the responsiveness of the opening/closing member 790 can be improved and air pressure can be finely regulated. The fixing member 794 receives the compression coil spring 796 therein. A virtual extension of an inner surface of the outer wall of the opening/closing member 790 is caused to substantially correspond to that of an inner surface of the fixing member 794 in order to prevent the coil spring 796 from abnormally operating in such a manner that the coil spring is bent or caught upon movement of the opening/closing member 790.

Referring still to FIG. 3(a), a pressure-regulating plate 101 can be provided between the bottom of the fixing member 794 and a relevant contact surface of the compression coil spring 796. The pressure-regulating plate 101 is a thin disk with a hole 102 in the center thereof. An elastic force of the compression coil spring 796 can be controlled by the pressure-regulating plate 101. A plurality of overlapped pressure-regulating plates may be used according to a desired reference pressure.

The cover member 798 is to cover an outer portion of the bore. The cover member 798 comprises a cover plate 7981 and a sidewall 7983. A hole 104 is provided in the center of the cover plate 7981, and the cover member is tightly fitted into the bore so that the sidewall 7983 is in close contact with the wall surface of the bore 780. A rim portion of the cover plate extends slightly in a radial direction, is bent toward an open end of the cover member and then extends more slightly. An end 7985 of the rim portion of the cover plate is fitted into an annular groove 786 provided in the sidewall 64 of the body 62 so that the cover member 798 can be fixed to the body 62.

Referring again to FIGS. 1 and 2, the cover 80 covers an opening of the first cavity 68 of the body 62. The cover 80 comprises a solid material containing portion 84 provided in the center thereof, a coupling portion 86 at an outer periphery thereof, and a flat connection portion 82 for connecting them. The containing portion 84 is made by forming a dome-type wall protruding roundly from the connection portion 82. A containing space is defined in the containing portion 84. A boss 85 is provided in the center of the dome-type wall. At least the dome-type wall of the cover 80 for defining the containing portion is preferably constructed to be pliable enough to be deformed when a user exerts a force thereon with his/her finger. A thin partition or membrane 83 is attached to the flat connection portion 82 so as to cover the space defined in the containing portion 84. The partition can be torn by a predetermined pressure. By means of the partition 83, the space 81 defined in the containing portion 84 is provided as a separate space isolated from the first cavity 68 containing the liquid material 72. The space 81 contains a disk-type or cylindrical solid material 810 therein.

The solid material 810 mainly consists of a material that can react with liquid material 72 in the first cavity 68 and produce gas. An embodiment of the present invention uses a pellet-type formulation which is produced by preparing a pellet through extrusion molding of a composition comprising a major amount of sodium carbonate ($Na_2CO_3$), a minor amount of gelatin and an additional minor amount of synthetic resin that hardly reacts with an acid, coating the pellet with a resin that hardly reacts with the acid, and forming a hole in the center of the coated pellet.

The coupling portion 86 shown on an enlarged scale in FIG. 2 comprises a peripheral wall that includes an inner sidewall 860 bent perpendicularly to the flat connection portion 82 and extending therefrom by about a distance generally corresponding to the height of the containing portion 84, an extension wall 861 bent perpendicularly to the inner sidewall 860 and extending therefrom radially outward by a small distance, and an outer sidewall 862 bent perpendicularly to the extension wall 861 and extending therefrom to a position corresponding to the flat connection portion 82. An end portion of the outer sidewall 862 is provided with an inner wall depression portion 863 constructed in such a manner that an inner wall surface of the end portion of the outer sidewall is depressed radially outward. The sidewall 64 of the body 62 is fitted into a space between the inner sidewall 860 and the outer sidewall 862 and the outer sidewall 862 of the cover 80 is then bonded to a wall surface of the cover insertion portion 641*b* of the body 62 through an adhesive. Generally, the bonding is achieved by applying the adhesive to the wall surface of the cover insertion portion 641*b* of the body 62 and fitting the cover 80 there around. During this process, some of the adhesive may be pushed and moved by the outer sidewall 862 of the cover 80. The pushed and moved adhesive is collected in the inner wall depression portion 863 of the cover 80 or in a small space 864 where the groove 643 of the stepped portion 626 of the body 62 is formed. Further, since the adhesive pushed and moved into the space 864 also cures, a surplus of the adhesive cannot flow out. Thus, the bonded portions are clean and the sealing effect is considerably improved. A sealing ring 865 with an "L-shaped" cross section is interposed between the outer wall depression portion 642*b* at the end of the cover insertion portion 641*b* and the outer sidewall 862 and extension wall 861 of the cover 80. In a state where the body 62 and the cover 80 are coupled with each other, an upper end of the sheet 70 is exposed to a space defined between the sidewall 64 of the body 62 and the inner sidewall 860 of the cover 80. This space is a space for allowing gas produced through a reaction between the solid material 810 and the liquid material 72 to sufficiently come into contact with the sheet 70.

Now, the operation of the liquid supply apparatus will be described in detail. Referring to FIG. 1, a predetermined amount of medicine is infused into the cylinder 20 through the supply valve member 92 in a state (not shown) where the piston 40 is in contact with the head portion 22 of the cylinder 20. Then, the piston 40 is pushed rearward and the cylinder 20 is filled with the medicine. In this state, when the containing portion 84 of the cover 80 is pressed, the partition 83 is torn as shown in FIG. 7, and the solid material 810 then falls into the liquid material 72 in the first cavity 68. Referring to FIGS. 2 and 7, when the solid material 810 mainly comprising sodium carbonate comes into contact with the liquid material 72 of L-tartaric acid, they chemically react and generate carbon dioxide gas. The generated gas passes through the gas-permeable membrane 701 of the sheet 70 and flows into the one-way valve 760 via the aperture 705 of the film 703 and the through-hole 660 of the partition 66. The pursed end of the one-way valve 760 is opened by means of the gas pressure, and then, the gas flows into the cylinder 20. The piston is pushed by the gas pressure gas flowing into the cylinder 20 so that the medicine is supplied.

Next, the operation of the pressure regulator will be described with reference to FIGS. 3(*a*) and (*b*). FIG. 3(*a*) shows a state where the opening/closing member 790 is closed. In this state, the gas pressure in the cylinder is transmitted to the opening/closing member 790 through the connection passage 782. If the gas pressure is below the reference pressure, the opening/closing member 790 cannot overcome the elastic force of the compression coil spring 796, and thus, remains in the closed state while being in contact with the sealing ring 79. If the gas pressure transmitted through the connection passage 782 is beyond the reference pressure, the gas pressure overcomes the elastic force of the compression coil spring 796 and pushes the opening/closing member 790. Thus, the opening/closing member 790 is opened while being separated from the sealing ring 79. This state is shown in FIG. 3(*b*). When the opening/closing member 790 is opened, the gas flows into the fixing member 794 through the passage 785 shown in FIG. 6. Consequently, the gas is exhausted to the outside through the hole 799 of the fixing member 794 and the hole 104 of the cover member 798, and thus, the gas pressure in the cylinder is lowered. When the gas pressure in the cylinder is restored to the reference pressure, the opening/closing member is closed to preserve the gas pressure in the cylinder. By doing so, a constant gas pressure is maintained in the cylinder to cause the piston to move at a constant speed.

Figure 8:
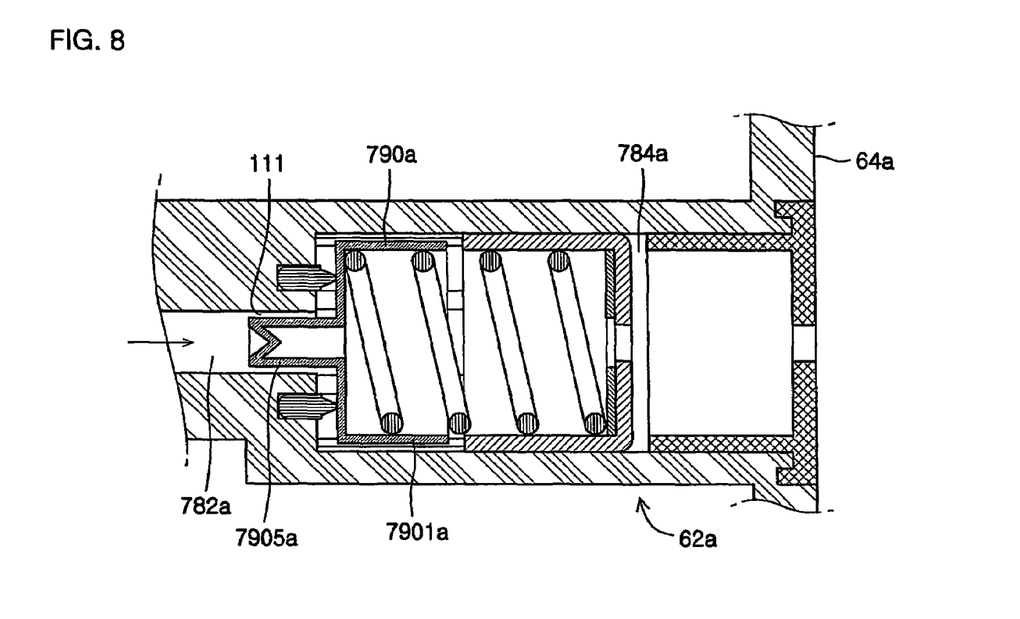
FIG. 8 is a sectional view of a pressure regulator according to another embodiment of the present invention.
Figure 9:
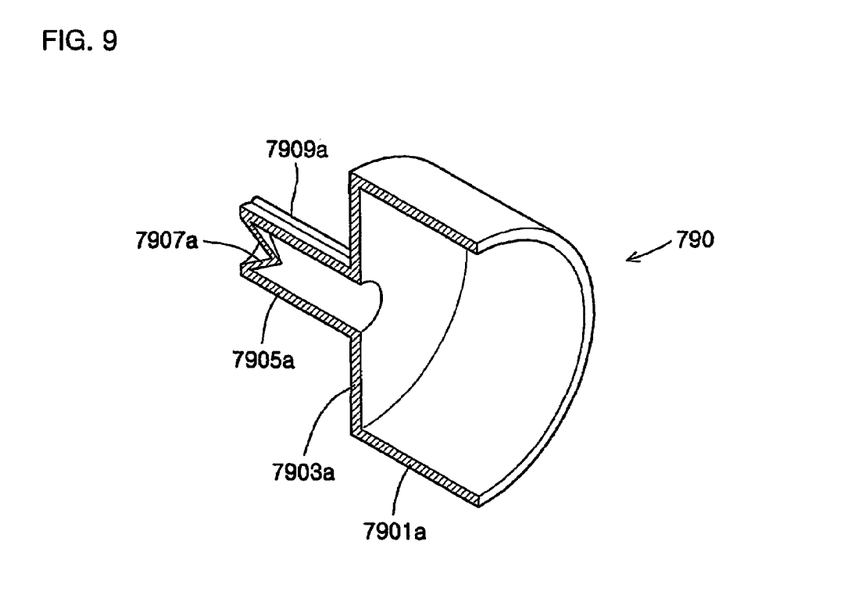
FIG. 9 is a sectional perspective view of an opening/closing member of the pressure regulator of FIG. 8.

FIGS. 8 and 9 are views showing a pressure regulator according to another embodiment of the present invention. Referring to FIG. 8, the pressure regulator is the same as that shown in FIG. 3 in their constitutions except that an opening/closing member 790*a* with a different configuration is used and the cylindrical protruding tube 202 shown in FIG. 3 is eliminated. The opening/closing member 790*a* of this embodiment comprises a cylindrical outer wall 7901*a*, a bottom wall 7903*a*, a cylindrical protruding wall 7905*a* extending outward from the center of the bottom wall, and a conical slant wall 7907*a* formed at an end of the protruding wall 7905*a* to extend thereinto. Three ridges 7909*a* are formed longitudinally on an outer surface of the protruding wall 7905*a* (the present invention is not limited to the three ridges). Each of the ridges 7909*a* has a semicircular cross section of which vertex is in contact with an inner surface of the connection passage 782*a*. The movement of the opening/closing member 790*a* is guided by means of the ridges 7909*a*. Since the other configurations are the same as the embodiment shown in FIG. 3, the detailed description thereof will be omitted.

Figure 10:
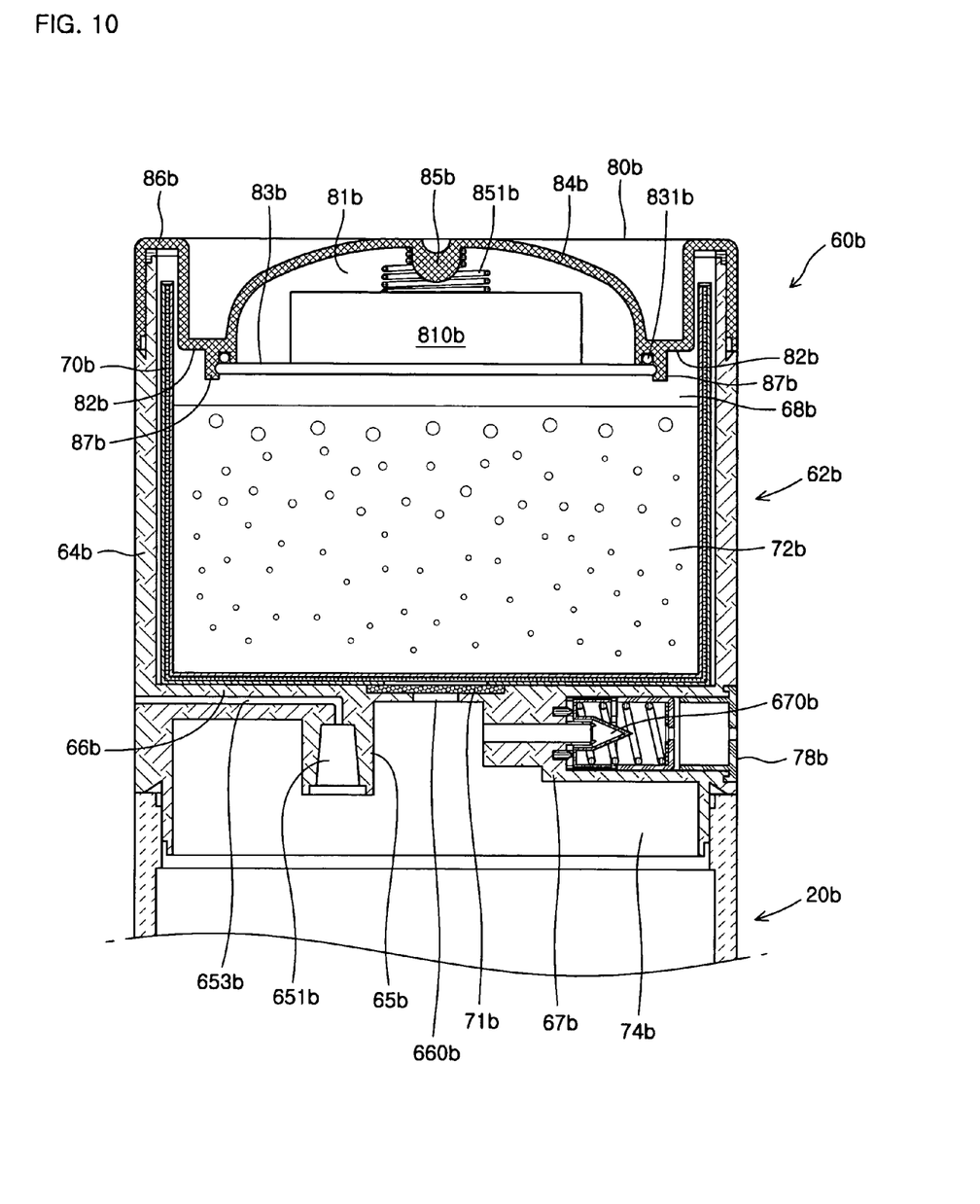
FIG. 10 is a sectional view of a gas supply apparatus according to a further embodiment of the present invention.
Figure 11:
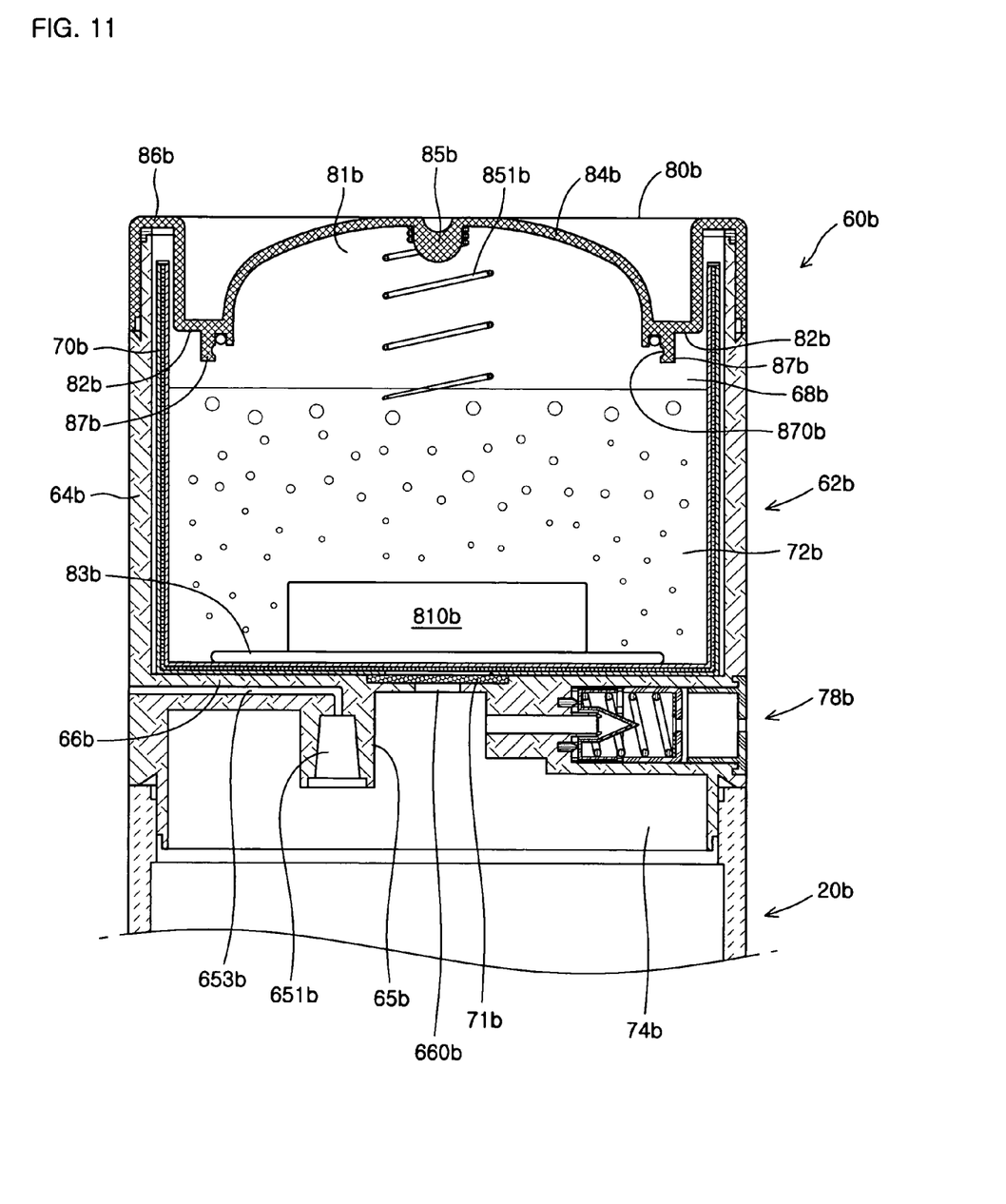
FIG. 11 is a view showing the operation of the gas supply apparatus of FIG. 10.

FIGS. 10 and 11 are views showing a gas supply apparatus according to a further embodiment of the present invention. Referring to these figures, the gas supply apparatus 60*b* comprises a body 62*b*, and a cover 80*b* for covering an end of the body 62*b*. The body 62*b* comprises a cylindrical sidewall 64*b* and a partition 66*b* disposed therein. The body 62*b* is divided into a first cavity 68*b* directed to the cover 80*b* and a second cavity 74*b* directed to the cylinder 20*b* by the sidewall 64*b* and the partition 66*b*. The first and second cavities 68*b*, 74*b* communicate with each other through a through-hole 660*b* provided in the center of the partition 66*b*. The first cavity 68*b* is provided with a flexible multi-layered gas-permeable sheet 70*b* over the inner periphery and bottom of the first cavity. The configuration of the sheet is the same as the embodiment shown in FIG. 2. A portion of the partition 66*b* adjacent to the through-hole 660*b* below the sheet 70*b* is provided with a recess. One gas-permeable but liquid-impermeable membrane 71*b* is disposed within the recess. The membrane 71*b* additionally prevents the any leakage of a liquid material 72b that may occur upon breakage of the sheet 70b.

Referring to FIG. 10, a raised portion is provided in the partition 66b at a side of the second cavity, and the raised portion 67b is provided with a bore 670b in which a pressure regulator 78b is mounted. The bore 670b communicates with the second cavity 74b. Since the configuration of the pressure regulator 78b shown in FIG. 10 is the same as the embodiment shown in FIG. 2, the detailed description thereof will be omitted.

On a side opposite to the pressure regulator 78b, there is provided a structure through which external air can flow into the second cavity 74b but gas cannot leak out. Referring to FIG. 10, the partition 66b is provided with a protruding boss 65b. The boss 65b is formed with a hole in which a one-way valve 651b is mounted. The partition 66b is formed with a passage 653b communicating with the outside through the hole. The one-way valve 651b allows air to flow from the outside into the second cavity 74b but prevents the gas from flowing in the opposite direction. In a state where an infusion medicine is not filled into the cylinder, if air within the cylinder 20b at the rear of the piston (not shown in FIG. 10) is contracted due to a change in temperature, its pressure is lowered. At this time, the outside air flows into the second cavity through the passage 653b and the one-way valve 651b. Therefore, it is possible to prevent the risk of unintentionally moving the piston rearward due to the contraction of gas in the cylinder.

Referring still to FIGS. 10 and 11, the cover 80b covers an opening of the first cavity 68b of the body 62b. The cover 80b comprises a solid material-containing portion 84b provided in the center thereof, a coupling portion 86b at an outer periphery thereof, and a flat connection portion 82b for connecting them. The containing portion 84b is made in the form of a dome protruding roundly from the connection portion 82b. A containing space is defined in the containing portion 84b, and a boss 85b is provided in the center of the containing portion. The connection portion 82b is provided with an annular support wall 87b extending circumferentially. An inner surface of the support wall 87b is provided with an annular groove 870b extending circumferentially. A partition 83b is fitted into and fixed to the groove 870b. A sealing ring 831b is interposed between the partition 83b and the connection portion 82b.

An inner space 81b defined in the containing portion 84b is isolated from the first cavity 68b containing the liquid material by means of the partition 83b. A disk-type or cylindrical solid material 810b is contained in the isolated space 81b. Meanwhile, the solid material 810b is urged against the partition 83b by means of an elastic member 851b. One end of the elastic member 851b is fixed to the boss 85b. Since other configurations that have not yet been described among the configurations of the gas supply apparatus 60b shown in FIG. 10 are the same as the embodiment shown in FIG. 2, the detailed description thereof will be omitted.

Referring to FIG. 11, when the containing portion 84b of the cover of the gas supply apparatus 60b is pressed, the partition 83b is separated from the cover 80b by means of the pressing force. At this time, the solid material is moved into the liquid material and a chemical reaction begins to occur therebetween. The elastic member 851b assists the solid material to completely escape from the containing space.

This configuration of the elastic member can be employed even in the case where the partition shown in FIG. 2 is used. The elastic member assists the solid material to effectively move via the torn partition.

Although the present invention has been illustrated and described with reference to the exemplified embodiments of the present invention, the present invention is not limited thereto. It should be understood that various changes and modifications can be made thereto without departing from the spirit and scope of the present invention.

The invention claimed is:

1. A liquid supply apparatus, comprising:
   an elongated cylinder including a head portion with an opening, and an open rear portion;
   a piston which is inserted into the cylinder and hermetically divides an inner space of the cylinder into a liquid compartment on the side of the head portion and a gas compartment on the side of the rear portion;
   a gas supply apparatus connected to the rear portion of the cylinder and constructed to supply the gas compartment with gas such that the piston is moved toward the head portion when the gas is supplied to the gas compartment;
   wherein the piston comprises a body and a sealing ring which surrounds the body and is in contact with an inner surface of the cylinder, and the sealing ring comprises an inner base fixed to the body and an outer wing which is connected to the base and is in contact with the inner surface of the cylinder;
   wherein the piston comprises at least two sealing rings, and the outer wing of one of the sealing rings on a side of the liquid compartment extends toward the liquid compartment and the outer wing of the other sealing ring on a side of the gas compartment extends toward the gas compartment; and
   wherein a sealing ring on a side of the liquid compartment and a sealing ring on a side of the gas compartment are sealing rings with a substantially identical dimension, and a radius of the bottom of the groove in the piston body into which the sealing ring on the side of the gas compartment is fitted is larger than that of the bottom of the groove into which the sealing ring on the side of the liquid compartment is fitted.

2. The liquid supply apparatus as claimed in claim 1, wherein the outer wing is inclined with respect to a wall of the cylinder.

3. The liquid supply apparatus as claimed in claim 1 or 2, wherein the body is provided with an annular groove, and the base of the sealing ring is fitted into the groove.

4. The liquid supply apparatus as claimed in claim 1 or 2, wherein the outer wing is configured such that a tip thereof does not extend beyond a distal end of the base.

5. The liquid supply apparatus as claimed in claim 1, wherein the head portion of the cylinder includes a truncated conical projection extending into the cylinder, the projection is formed with an opening, and the piston is provided with a truncated conical recess for accommodating the projection.

6. The liquid supply apparatus as claimed in claim 1, wherein the gas supply apparatus comprises an outer wall and a partition connected to the outer wall so as to define a gas supply chamber by the outer wall and the partition, the gas compartment of the cylinder and the gas supply chamber are divided by the partition, and the partition is provided with a through-hole through which the gas supply chamber and the gas compartment communicate with each other.

7. The liquid supply apparatus as claimed in claim 6, wherein the outer wall and the rear portion of the cylinder are fitted into or around and coupled with each other, and an annular groove is provided in one of fitted contact surfaces thereof, whereby upon coupling of the outer wall and the rear portion of the cylinder using an adhesive, a surplus of the adhesive is received by the annular groove.

8. The liquid supply apparatus as claimed in claim 6, wherein the outer wall comprises an insertion portion tightly fitted into the cylinder and bonded to an inner surface of the cylinder using an adhesive, an exposed portion exposed outside of the cylinder, and a stepped portion connected to an outer wall of the exposed portion radially outward from an outer wall of the insertion portion, and an edge between the insertion portion and the stepped portion is provided with an annular groove.

9. The liquid supply apparatus comprising:
- an elongated cylinder including a head portion with an opening, and an open rear portion;
- a piston which is inserted into the cylinder and hermetically divides an inner space of the cylinder into a liquid compartment on the side of the head portion and a gas compartment on the side of the rear portion;
- a gas supply apparatus connected to the rear portion of the cylinder and constructed to supply the gas compartment with gas such that the piston is moved toward the head portion when the gas is supplied to the gas compartment;
- wherein the gas supply apparatus comprises an outer wall and a partition connected to the outer wall, and the partition of the gas supply apparatus is provided with a bore through which the gas compartment and the outside of the cylinder communicate with each other, and the gas supply apparatus further comprises a pressure regulator provided in the bore;
- wherein the bore is cylindrical and connected to the gas compartment through a connection passage formed in the bottom of the bore, and
- the pressure regulator comprises:
- a sealing ring which surrounds the connection passage, is fixed to the bottom, and has an end protruding from the bottom,
- an opening/closing member including a contact wall with a contact surface which selectively comes into contact with or is separated from the end of the sealing ring, an inner wall axially extending from a central portion of the contact wall, and a conical slant wall protruding from an end of the inner wall to a side opposite to the connection passage, thereby moving in an axial direction of the bore, and
- an elastic member for urging the opening/closing member toward the sealing ring.

10. The liquid supply apparatus as claimed in claim 9, wherein a protruding tube surrounding the connection passage and axially protruding from the bottom is provided in the bore, and the inner wall of the opening/closing member surrounds the protruding tube.

11. The liquid supply apparatus as claimed in claim 10, wherein a guide structure for linear movement of the opening/closing member is provided between the protruding tube or the connection passage and the inner wall of the opening/closing member.

12. The liquid supply apparatus as claimed in claim 9, wherein the opening/closing member farther comprises an axially extending outer wall, and a guide structure for linear movement of the opening/closing member is provided between the outer wall and the bore.

13. The liquid supply apparatus as claimed in claim 9, wherein a stroke of the opening/closing member is limited to no more than 2 mm.

14. The liquid supply apparatus as claimed in any one of claims 9 to 13, wherein the sealing ring is fixed by being fitted into a groove formed in the bottom, and a tip of a portion of the sealing ring protruding from the groove is rounded.

15. The liquid supply apparatus as claimed in claim 6, wherein the gas supply chamber comprises a first chamber for containing a liquid material and a second chamber for containing a solid material which generates gas through a reaction with the liquid material, and a breakable separation structure is provided between the first and second chambers.

16. The liquid supply apparatus as claimed in claim 15, wherein an elastic member for urging the solid material toward the separation structure is provided in the second chamber.

17. The liquid supply apparatus as claimed in claim 15, wherein the separation structure comprises a first partition which surrounds a passage between the first and second chambers and is provided with an annular groove, and a second partition of which a rim is fitted into the annular groove of the first partition.

18. The liquid supply apparatus as claimed in claim 17, wherein a sealing ring is provided between the first and second partitions.

19. The liquid supply apparatus as claimed in any one of claims 15 to 18, wherein the outer wall further comprises a cover as a separate member, and the second chamber is defined in the cover.

20. The liquid supply apparatus as claimed in claim 19, wherein the cover comprises a peripheral wall fitted around the outer wall, and an annular groove is provided in one of fitted contact surfaces thereof, whereby upon coupling of the cover and the outer wall using an adhesive, an adhesive receiving space for collecting and receiving a surplus of the adhesive is provided.

21. The liquid supply apparatus as claimed in claim 19, wherein the cover comprises a peripheral wall and an inner sidewall extending parallel to and spaced apart from the peripheral wall at an outer periphery of the cover, whereby an end of a sheet for filtering gas is placed between the peripheral wall and the inner sidewall.

* * * * *